US 8,515,545 B2

(12) United States Patent
Trier

(10) Patent No.: US 8,515,545 B2
(45) Date of Patent: Aug. 20, 2013

(54) CURRENT STEERING NEUROSTIMULATOR DEVICE WITH UNIDIRECTIONAL CURRENT SOURCES

(75) Inventor: Stephen C. Trier, Mayfield Heights, OH (US)

(73) Assignee: Greatbatch Ltd., Clarence, NY (US)

( * ) Notice: Subject to any disclaimer, the term of this patent is extended or adjusted under 35 U.S.C. 154(b) by 95 days.

(21) Appl. No.: 13/098,071

(22) Filed: Apr. 29, 2011

(65) Prior Publication Data

US 2012/0277822 A1  Nov. 1, 2012

(51) Int. Cl.
*A61N 1/00* (2006.01)
(52) U.S. Cl.
USPC .......................................................... 607/59
(58) Field of Classification Search
USPC .............................................. 607/39–59, 63
See application file for complete search history.

(56) References Cited

U.S. PATENT DOCUMENTS

| | | |
|---|---|---|
| 5,895,416 A | 4/1999 | Barreras, Sr. et al. |
| 6,181,969 B1 | 1/2001 | Gord |
| 6,219,580 B1 | 4/2001 | Faltys et al. |
| 6,393,325 B1 | 5/2002 | Mann et al. |
| 6,516,227 B1 | 2/2003 | Meadows et al. |
| 6,553,263 B1 | 4/2003 | Meadows et al. |
| 6,895,280 B2 | 5/2005 | Meadows et al. |
| 7,444,181 B2 | 10/2008 | Shi et al. |
| 7,493,404 B2 | 2/2009 | Weber |
| 7,622,988 B2 | 11/2009 | Denison et al. |
| 7,747,318 B2 | 6/2010 | John et al. |
| 7,769,462 B2 | 8/2010 | Meadows et al. |
| 7,801,615 B2 | 9/2010 | Meadows et al. |
| 7,805,197 B2 | 9/2010 | Bradley |
| 7,831,307 B1 | 11/2010 | Moffitt |
| 2001/0031909 A1 | 10/2001 | Faltys et al. |
| 2005/0267546 A1 | 12/2005 | Parramon et al. |
| 2007/0156203 A1* | 7/2007 | Varrichio et al. ............... 607/59 |
| 2008/0269630 A1 | 10/2008 | Denison et al. |
| 2009/0082691 A1 | 3/2009 | Denison et al. |

(Continued)

FOREIGN PATENT DOCUMENTS

WO  WO 00/00251  1/2000
WO  WO 2007/127443 A2  11/2007

(Continued)

OTHER PUBLICATIONS

European Search Report in European Patent Application No. 12166020.3, dated Sep. 27, 2012, 5 pages.

(Continued)

*Primary Examiner* — Scott Getzow
(74) *Attorney, Agent, or Firm* — Haynes and Boone, LLP

(57) ABSTRACT

The present disclosure provides a medical device that includes a neurostimulator. The neurostimulator includes one or more channels. Each channel includes a digitally-controlled switch coupled to a voltage source. The switch is in one of an "on" state and an "off" state in response to a first control signal. Each channel also includes a digitally-controlled current sink coupled to the switch. The current sink is coupled between the switch and the voltage source. The current sink draws a variable amount of electrical current in response to a second control signal. Each channel further includes a conductor coupled to the switch and the current sink. The conductor is configured to be coupled to an electrode that is operable to deliver the electrical current drawn by the current sink to a target tissue area.

21 Claims, 12 Drawing Sheets

(56) References Cited

U.S. PATENT DOCUMENTS

| | | | |
|---|---|---|---|
| 2010/0069768 A1 | 3/2010 | Min et al. | |
| 2010/0114202 A1 | 5/2010 | Donofrio et al. | |
| 2010/0204766 A1* | 8/2010 | Zdeblick et al. | 607/119 |
| 2010/0280577 A1* | 11/2010 | Roy et al. | 607/62 |
| 2012/0296391 A1 | 11/2012 | Trier et al. | |

FOREIGN PATENT DOCUMENTS

| | | |
|---|---|---|
| WO | WO 2010/033610 A1 | 3/2010 |
| WO | WO-2010/055421 | 5/2010 |
| WO | WO 2010/065761 A2 | 6/2010 |
| WO | WO 2011/014909 A1 | 2/2011 |
| WO | WO 2012/088482 A1 | 6/2012 |

OTHER PUBLICATIONS

European Search Report in European Application No. 12173231.7, mailed Oct. 15, 2012, 6 pages.

* cited by examiner

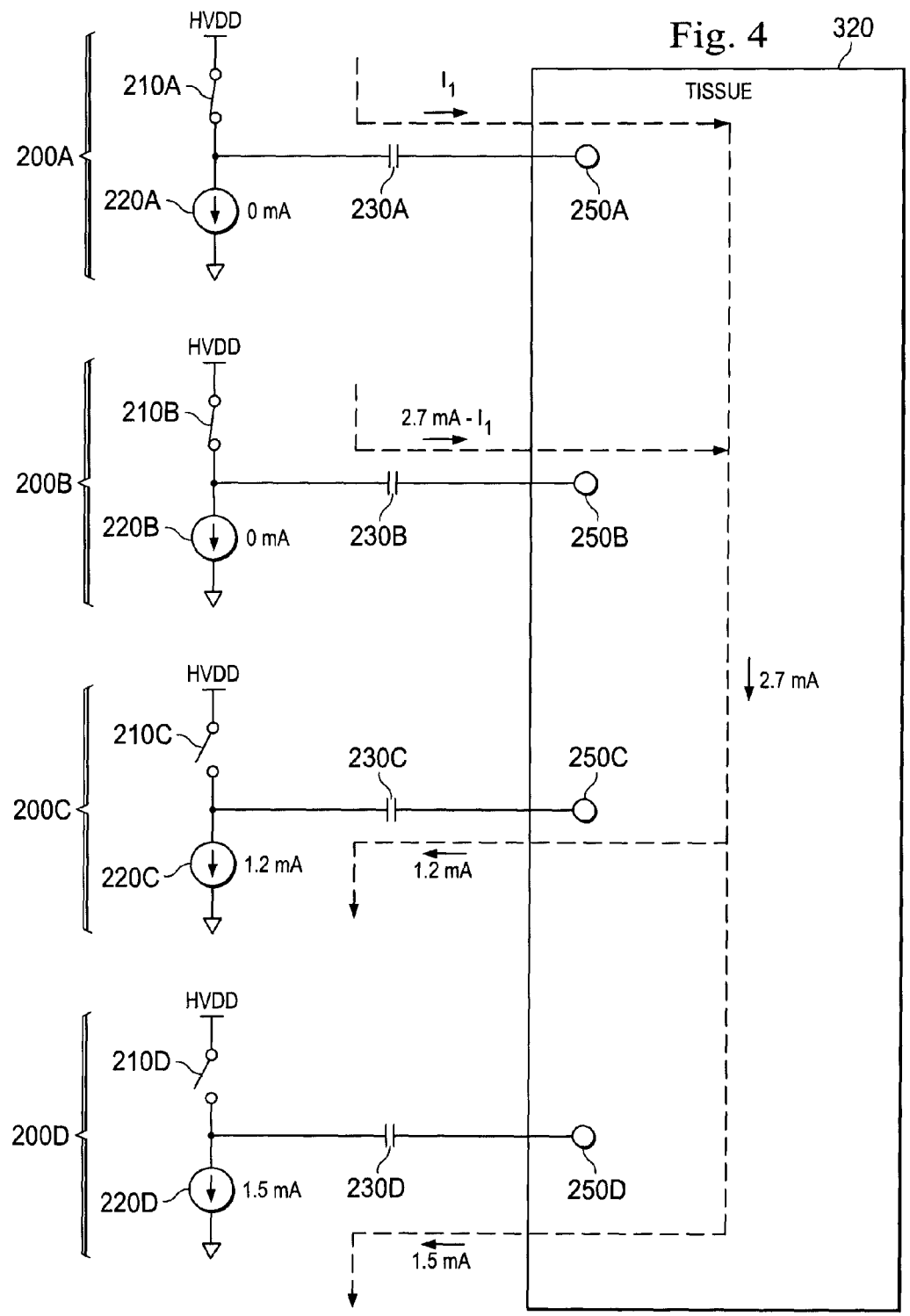

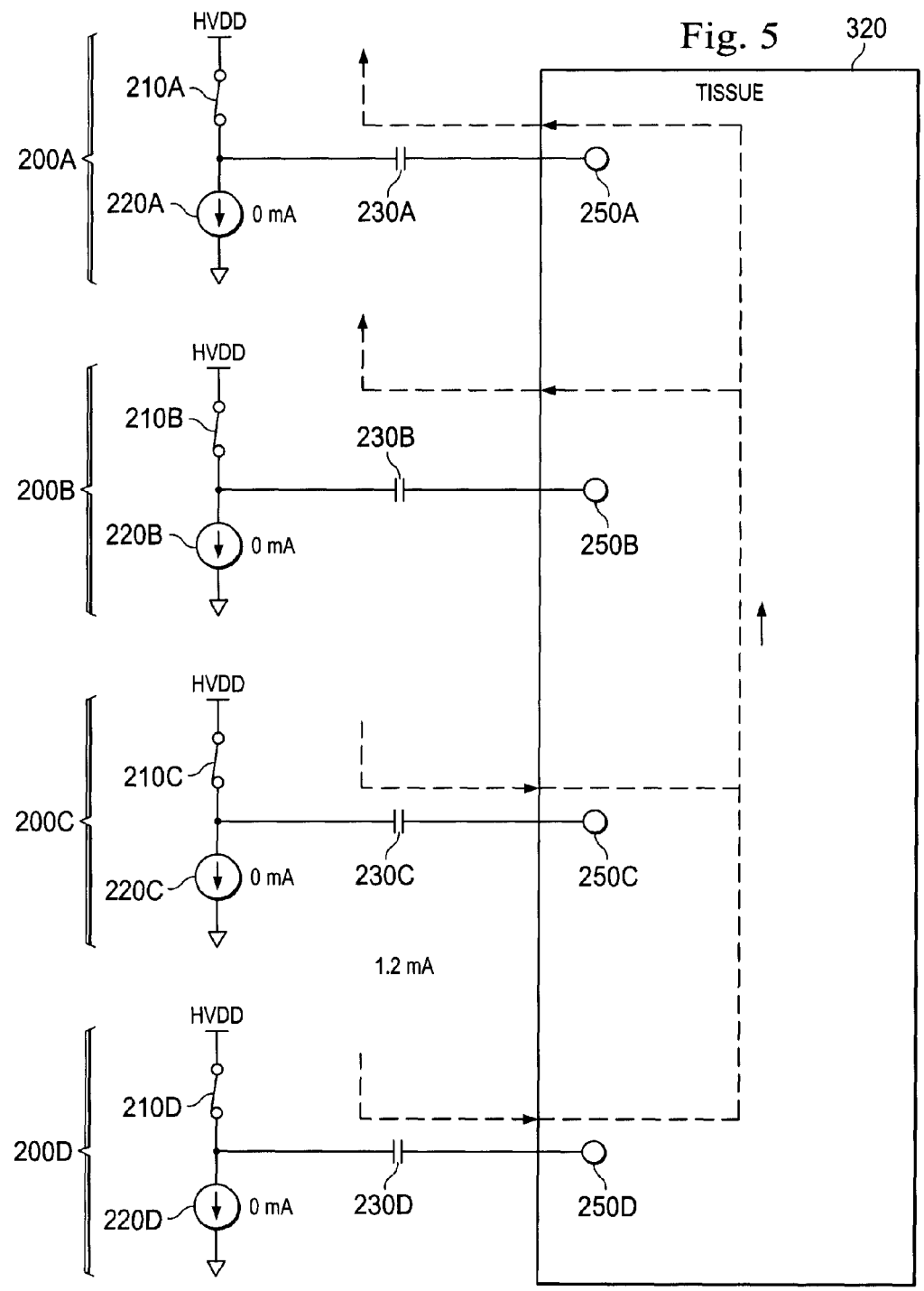

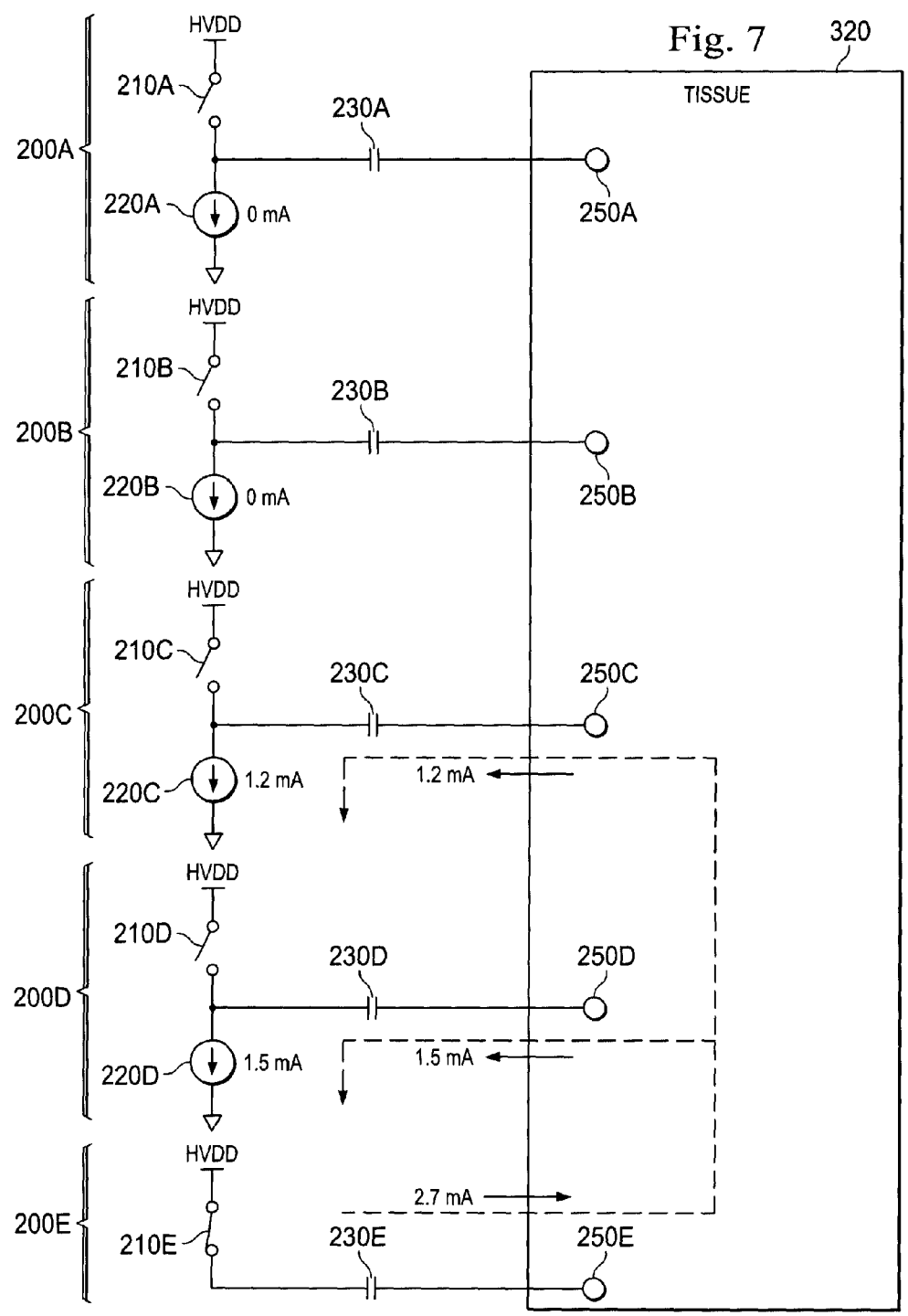

CURRENT STEERING NEUROSTIMULATOR DEVICE WITH UNIDIRECTIONAL CURRENT SOURCES

BACKGROUND

As medical device technologies continue to evolve, neurostimulator devices have gained much popularity in the medical field. Neurostimulator devices are electrically-powered devices (e.g., battery-powered) that are designed to deliver electrical stimulation to a patient. Through proper electrical stimulation, the neurostimulator devices can provide pain relief for patients. The medically accepted mechanism for pain relief is known as "gate control theory," which theorizes that the nervous system has a "gate" that closes and prevents the passage of pain signals if it is presented with sufficiently strong sensory signals. As a result, the patient may feel only a tingly sensation—also known as paresthesia—instead of pain in the area that is stimulated.

A typical neurostimulator device may include one or more integrated circuit chips on which the control circuitry and neurostimulation circuitry are built. The neurostimulator device may also include a plurality of electrodes that are in contact with different areas of a patient's body. Controlled by the control circuitry, the electrodes are each capable of delivering electrical stimulation to their respective target contact areas. Thus, the patient can use the neurostimulator device to stimulate areas in a localized manner.

Although neurostimulator devices have been proven to be useful, existing neurostimulator devices may still suffer from one or more shortcomings. For example, many existing neurostimulator devices can turn on and off each electrode, but they lack the capability to individually control the amount of electrical stimulation given by each electrode. As another example, some existing neurostimulator devices may require a large number of transistors to implement the neurostimulation circuitry. These transistors consume a significant amount of integrated circuit chip area and consequently drive up the fabrication costs of neurostimulator devices.

Therefore, while existing neurostimulator devices have been generally adequate for their intended purposes, they have not been entirely satisfactory in every aspect.

SUMMARY

One of the broader forms of the present disclosure involves an electrical stimulation apparatus. The apparatus includes: a power source; a programmable switch having a first terminal and a second terminal, wherein the first terminal is coupled to the power source; a unidirectional current source coupled to the second terminal of the switch, the unidirectional current source having a tunable current level; and a lead conductor coupled to the second terminal of the switch and the unidirectional current source, wherein the lead conductor is operable to deliver current drawn from the unidirectional current source through an electrode contact configured for contact with a living body.

Another one of the broader forms of the present disclosure involves a medical device. The medical device contains a neurostimulator that includes one or more implantable channels. Each channel includes: a digitally-controlled switch coupled to a voltage source, wherein the switch is in one of: an "on" state and an "off" state in response to a first control signal; and a digitally-controlled current sink coupled to the switch, wherein the current sink draws a variable amount of electrical current in response to a second control signal. In one aspect, the device further includes an electrode coupled to the switch and the current sink, wherein the electrode delivers the electrical current drawn by the current sink to a target tissue area.

Yet one more of the broader forms of the present disclosure involves a method. The method includes providing a neurostimulator having different first and second channels, the first channel including a first tunable unidirectional current source, the first and second channels also including: respective first and second switches each coupled to a power supply, wherein the first current source is coupled to the power supply through the first switch; and respective first and second electrodes coupled to the first and second switches, respectively. The method also includes entering a stimulation phase by: opening the first switch; closing the second switch; and tuning the first current source in a manner such that it sinks a programmable amount of electrical current. The method also includes entering a recovery phase by: closing both the first and second switches; and tuning the first current source in a manner such it does not sink any electrical current.

Another one of the broader forms of the present disclosure involves an electrical stimulation device. The electrical stimulation device includes a voltage supply means for delivering a steady voltage; a switching means for selectively opening and closing a circuit path coupled to the voltage supply means; a current sink means for sinking a programmably-adjustable amount of current, the current sink means being coupled to the voltage supply means through the switching means; and a conductor means for stimulating a living body, the conductor means being coupled to both the switching means and the current sink means.

Yet another one of the broader forms of the present disclosure involves an electrical stimulation device. The electrical stimulation device includes an anodic channel that includes an anode electrode coupled to a steady voltage supply; and a cathodic channel that includes a current sink that sinks a programmably-determined amount of current and a cathode electrode coupled to the current sink; wherein the anode electrode and the cathode electrode are both implemented on a lead that is operable to carry out electrical stimulation of a neural tissue.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 4-5 are simplified circuit level views of a plurality of channels of a neurostimulator device in a stimulation phase and a recovery phase of an operation, respectively.

FIGS. 7-8 are simplified circuit level views of a plurality of channels of a neurostimulator device in a stimulation phase and a recovery phase of an operation, respectively, according to an alternative embodiment of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Figure 1:
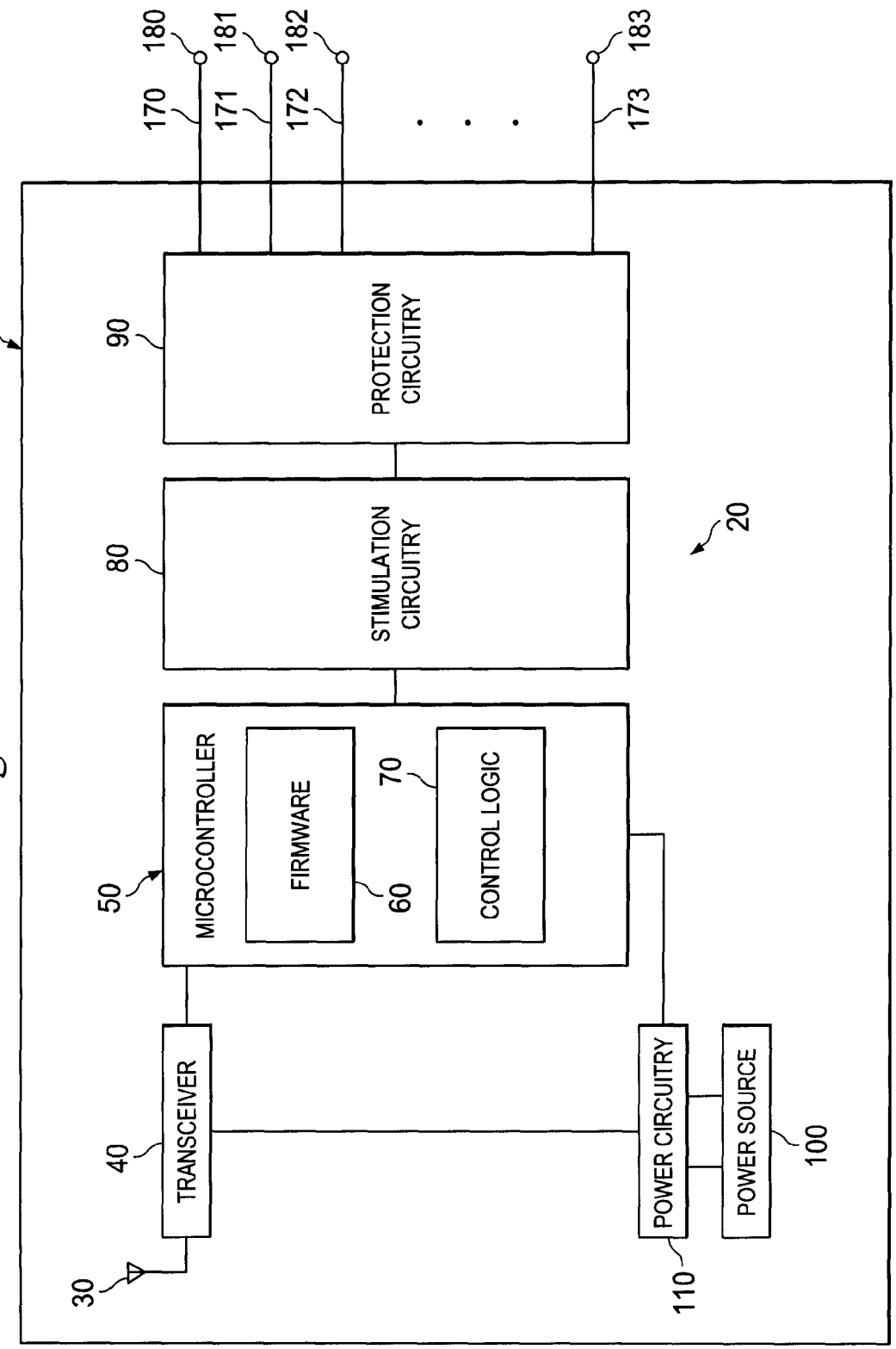
FIG. 1 is a simplified diagrammatic view of an embodiment of a neurostimulator device.

FIG. 1 is a simplified diagrammatic view of an embodiment of a neurostimulator device 20. The neurostimulator device 20 includes an antenna 30 and a transceiver 40 coupled to the antenna 30. The antenna 30 is capable of sending signals to an external device and receiving signals from the external device. The transceiver 40 contains transmitter circuitry and receiver circuitry that together carry out digital communication with the external device. In an embodiment, the signals are transmitted and received at Radio Frequencies (RF).

The neurostimulator device 20 includes a microcontroller 50 that is coupled to the transceiver 40. Based on the output of the transceiver 40 (i.e., the input received from the external device), the microcontroller 50 runs firmware 60, which is a control program, to operate control logic 70. The firmware 60 includes dedicated low-level software code that is written for a specific device, in this case the control logic 70. The control logic 70 includes digital circuitry that is implemented using a plurality of transistors, for example Field Effect Transistors (FETs). In the embodiment shown in FIG. 1, the firmware 60 and the control logic 70 are integrated into the microcontroller 50. In alternative embodiments, the firmware 60 or the control logic 70 may be implemented separately from the microcontroller 50.

The neurostimulator device 20 includes stimulation circuitry 80 that receives the output of the microcontroller 50. In an embodiment, the stimulation circuitry 80 is implemented on an Application Specific Integrated Circuit (ASIC) chip. The stimulation circuitry 80 includes electrical pulse generation circuitry. Based on the output of the microcontroller 50, the electrical pulse generation circuitry generates electrical pulses (signals) to a target tissue area. Various aspects of the pulse generation are described in detail in U.S. patent application Ser. No. 13/081,896, Titled "Charge Balancing For Arbitrary Waveform Generator & Neural Stimulation Application" and filed on Apr. 7, 2011, U.S. patent application Ser. No. 13/082,097, Titled "Arbitrary Waveform Generator & Neural Stimulation Application With Scalable Waveform Feature" and filed on Apr. 7, 2011, and U.S. patent application Ser. No. 13/081,936, Titled "Arbitrary Waveform Generator & Neural Stimulation Application" and filed on Apr. 7, 2011, each of which is hereby incorporated by reference in its entirety. Other aspects of the stimulation circuitry 80 will be discussed later in greater detail.

The neurostimulator device 20 also includes protection circuitry 90 that is coupled to the output of the stimulation circuitry 80. In an embodiment, the protection circuitry 90 includes direct-current (DC) blocking capacitors and other electrical transient suppression components. The protection circuitry 90 protects the patient's tissue from unwanted electrical signals. The protection circuitry 90 also protects the neurostimulator device 20 from undesirable external events such as electrostatic discharge, defibrillation, or electrocautery.

The neurostimulator device 20 also includes a power source 100 and power circuitry 110. In an embodiment, the power source 100 includes a battery. In another embodiment, the power source 100 includes a coil that is a part of a transformer (not illustrated). In that case, the transformer has a charging coil that is external to the neurostimulator device 20 and inductively coupled to the coil of the power source 100. The power source 100 therefore obtains energy from such inductive coupling to the charging coil. In some embodiments, the power source 100 may also include both a battery and a coil. The power source 100 provides electrical power to the power circuitry 110. The power circuitry 110 is coupled to the transceiver 40, the microcontroller 50, the stimulation circuitry 80. The power circuitry 110 supplies and regulates power to these coupled circuitries. In an embodiment, the power circuitry 110 is implemented on an ASIC device.

In an embodiment, the antenna 30, the transceiver 40, the microcontroller 50, the stimulation circuitry 80, the protection circuitry 90, the power source 100, and the power circuitry 110 are all contained within a hermetically-sealed housing 150 (which may also be referred to as a can). The housing 150 may also be considered a part of the neurostimulator device 20. The housing 150 may be made from titanium or another suitable durable and/or conductive material.

A plurality of conductors (also referred to as lead wires) 170-173 run from the internal circuitry through hermetic feedthroughs to one or more connectors mounted on the hermetic enclosure. The lead wires 170-173 plug into, and are removable from, those connectors. In another embodiment, the connectors are eliminated, and the lead wires 170-173 are directly and permanently connected to the hermetic feedthroughs. In some embodiments, the neurostimulator incorporates the electrode contacts into its outer surface. In such embodiments, the hermetic feedthroughs may be designed to incorporate an electrode contact in the tissue-facing side of each feedthrough, or may be designed to have insulated lead wires built into the neurostimulator housing, exterior to the hermetically-sealed enclosure, that carry signals between the hermetic feedthroughs and the electrode contacts. It is understood that the lead wires 170-173 are shown merely as examples, and that an alternative number of lead wires may be implemented, for example 16 or 24 lead wires.

Electrode contacts 180-183 (also referred to as electrodes) are coupled to the lead wires 170-173. The electrode contacts 180-183 are implanted in different areas of a patient's body, where electrical stimulation is desired. In an embodiment, an exterior portion of the housing 150 is also used as an electrode contact. In another embodiment, one or more electrode contacts can be incorporated into the design of a non-conductive housing 150. In any case, the electrode contacts may also be considered parts of the neurostimulator system.

In an embodiment, the neurostimulator device 20 is implemented as an Implanted Pulse Generator (IPG) device, in which case all the components shown in FIG. 1 are surgically implanted inside the patient's body. Outside the body, the neurostimulator device 20 can be programmed using a Clinician Programmer (not illustrated) or a Patient Programmer (not illustrated). The Clinician Programmer is used by medical personnel (such as doctors or nurses) or by others (such as sales representatives or the patient himself) to configure the neurostimulator device 20 for the particular patient and to define the particular electrical stimulation therapy to be delivered to the target area of the patient's body. The Patient Programmer is used by the patient himself to control the operation of the neurostimulator device 20. For example, the patient can alter one or more parameters of the electrical stimulation therapy, depending on the programming and the configuration of the neurostimulator device 20 as set by the Clinician Programmer.

In alternative embodiments, the neurostimulator device 20 can be implemented as an External Pulse Generator (EPG). In that case, only a portion of the neurostimulator system (for example the electrode contacts 180-183 and/or portions of the lead wires 170-173) is implanted inside the patient's body, while part or all of the neurostimulator device 20 remains outside the body. Other than their exact placements, the functionalities and the operations of the IPG and the EPG are similar. A medical device manufacturer may manufacture and provide the neurostimulator device 20 to a clinician or a patient. Clinicians may also provide the neurostimulator device to a patient. Some of the functionalities of the microcontroller 50 may be pre-programmed by the manufacturer or may be programmed by the clinician or patient.

Figure 2:
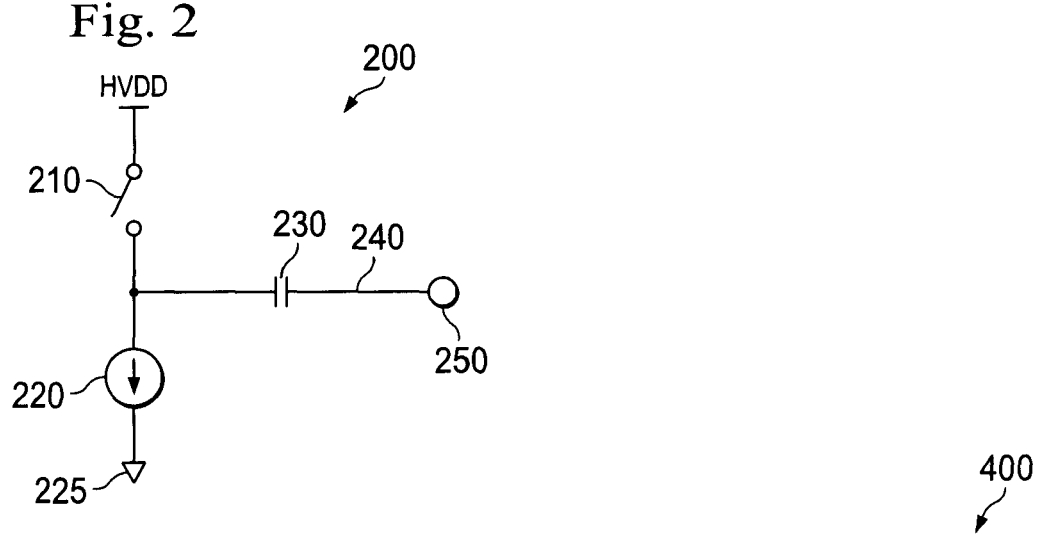
FIG. 2 is a simplified circuit level view of an embodiment of a channel of a neurostimulator device.

The neurostimulator device 20 is capable of varying the amount of electrical stimulation delivered to each of the electrode contacts 180-183. This is carried out by creating individually controllable electrical paths, or channels. Each channel includes one of the electrode contacts 180-183, one of the lead wires 170-173 coupled to the electrode contact, and respective portions of the protection circuitry 90 and respective portions of the stimulation circuitry 80. FIG. 2 illustrates a simplified circuit diagrammatic view of an example channel 200. The channel 200 includes a programmable switch 210, a current sink 220 (i.e., a unidirectional current source), a protective component 230, a lead wire 240, and an electrode contact 250.

The switch 210 is powered by a voltage source HVDD, which in an embodiment is a power supply rail and is supplied by the power circuitry 110 of FIG. 1. The voltage source HVDD produces a steady output voltage. The voltage source HVDD can also be programmably set to accommodate the tissue impedance of the patient. The programmability of the voltage source HVDD helps improve power efficiency and extend battery life. And although not shown in the simplified view of FIG. 2, the switch 210 is coupled to the microcontroller 50 of FIG. 1. The microcontroller 50 sends control signals to the switch 210 to either turn it on (where the switch is closed) or shut it off (where the switch is open). In an embodiment, the switch 210 is implemented with one or more transistors and is designed to have a low resistance when it is turned on.

The current sink 220 sinks electrical current to create an electric field in the target tissue area of the patient's body. The electric field generates neural signals that mask other neural signals. When the neurostimulator is used to treat pain, instead of feeling pain in the target tissue area, the patient feels a tingly sensation. One end of the current sink 220 is coupled to the switch 210, and the other end of the current sink 220 is coupled to a terminal 225. In an embodiment, the terminal 225 is tied to ground. In other embodiments, the terminal 225 may be tied to another voltage level or voltage reference.

Although not shown in the simplified view of FIG. 2, the current sink 220 is also coupled to the microcontroller 50 of FIG. 1. The microcontroller 50 sends control signals to the current sink 220 to vary its electrical current amplitude. In an embodiment, the current sink 220 is implemented with a plurality of transistors. The switch 210 and the current sink 220 are portions of the stimulation circuitry 80 of FIG. 1. The switch 210 and the current sink 220 will be discussed in more detail later in association with FIG. 3.

Still referring to FIG. 2, the protective component 230 is a part of the protection circuitry 90 of FIG. 1. As discussed above, among other things, the protection circuitry 90 protects the patient's tissue from unwanted electrical signals. These unwanted electrical signals include DC signals. If a DC component is present in the electrical stimulation (represented by a voltage or current waveform, for example) delivered, it will result in corrosion around the respective electrode contact and may potentially harm the patient's tissue near the electrode contact. Consequently, it is desirable for the neurostimulator device 20 to only deliver an alternating current (AC) electrical signal to the patient. For that to happen, the neurostimulator device 20 needs to filter out any DC component in the electrical signal. Thus, in the embodiment shown in FIG. 2, the protective component 230 is implemented as a DC-blocking capacitor. The DC-blocking capacitor has a capacitance in a range from about 0.05 microfarad (uF) to about 5 uF.

One end of the protective component 230 is coupled to the switch 210 and the current sink 220. As discussed above, the switch 210, the current sink 220, and the protective component 230 are all contained in the hermetically-sealed housing 150 of FIG. 1 according to one embodiment. The other end of the protective component 230 is coupled to the lead wire 240. In other words, the lead wire 240 extends out of the housing 150, for example through a feedthrough. The lead wire 240 includes a conductive material in an embodiment. In one embodiment, the lead wires may include a coupling mechanism for removably receiving a connector joining the elongated lead wires to the IPG, the lead wires having electrodes attached thereto. The coupling mechanism or the connector may be implemented inside or outside the housing 150.

The other end of the lead wire 240 is coupled to the electrode contact 250. The electrode contact 250 is planted at or near the target tissue area of the patient's body. The electrode contact 250 provides electrical stimulation (generated by the current sink 220) to the target tissue area. It is understood that the hermetically-sealed housing 150 of FIG. 1 may also serve as an electrode contact in some embodiments. Unlike the electrode contacts similar to the electrode contact 250, the housing 150 may be driven without a current sink similar to the current sink 220. Also, it is possible for the protective component 230 to be omitted from the housing 150.

Figure 3:
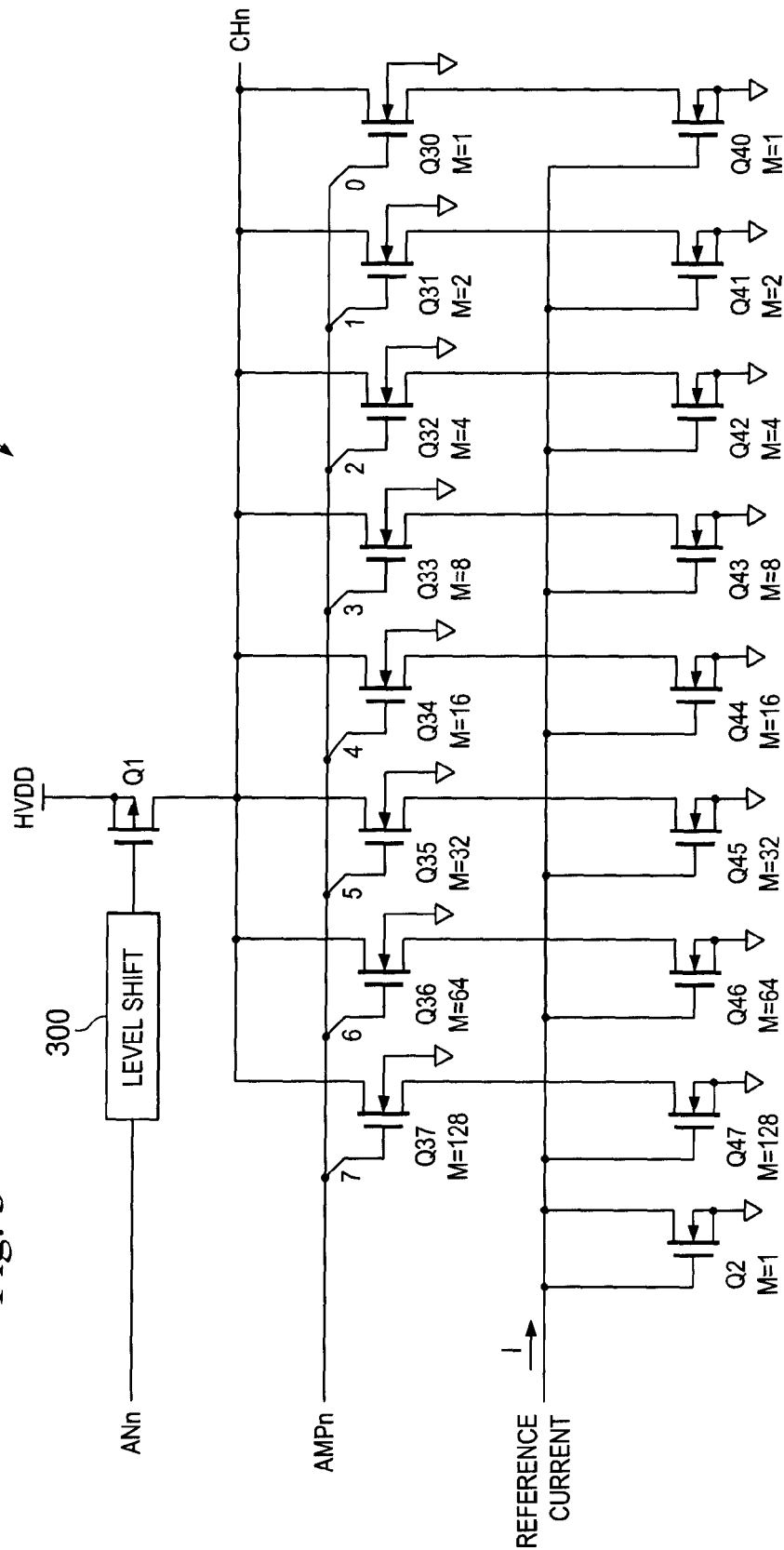
FIG. 3 is a simplified transistor level view of an embodiment of the channel of FIG. 2.

FIG. 3 is an example transistor circuit level view of the channel 200 of FIG. 2. The protective component 230, the lead wire 240, and the electrode contact 250 are omitted from FIG. 3 for the sake of simplicity. The channel 200 includes a plurality of transistor devices Q1-Q47. The transistor devices Q1-Q47 may each include one or more identical N-type FETs (NFETs) or P-type FETs (PFETs). In the embodiment shown in FIG. 3, Q1 is implemented with a PFET, and Q2 and Q30-Q47 are implemented with NFETs. In other embodiments, Q1 may be implemented with an NFET, Q2 and Q30-Q47 may be implemented with PFETs.

Each NFET or PFET includes a gate terminal, a source terminal, a drain terminal, and a body (also referred to as bulk or substrate) terminal. Depending on the voltage levels applied to each terminal, the FET turns "on" or "off." For ease of reference, the paragraphs below will refer to these terminals as being terminals of the transistor devices Q1-Q2 and Q30-Q47, instead of referring to them as terminals of the FETs of the transistor devices. Also for ease of reference, the gate terminal, the source terminal, the drain terminal, and the body terminal may be referred to as the gate, the source, the drain, and the body, respectively.

The letter "M" next to the transistor devices Q1-Q47 represents the number of identical FETs included in each transistor device. As examples, for the transistor device Q30, M=1, which indicates the transistor device Q30 includes only 1 FET. For the transistor device Q33, M=8, which indicates the transistor device Q33 includes 8 identical FETs. For the transistor device Q47, M=128, which indicates the transistor device Q47 includes 128 identical FETs. These identical FETs have their respective gates coupled together; their respective drains coupled together, their respective sources coupled together, and their respective bodies coupled together.

The switch 210 of FIG. 2 is implemented as the transistor device Q1. The source and body of the transistor device Q1 are coupled to the voltage source HVDD. The drain of the transistor device Q1 is coupled to the drains of the transistor devices Q30-Q37. The gate of the transistor device Q1 is coupled to receive a binary control signal ANn through a level shift device 300. The control signal ANn is generated by the control logic 70 of the microcontroller 50 of FIG. 1. The voltage level of the control signal ANn is within a standard voltage level range for typical logic circuitry, which may range from 0-5 volts. The HVDD voltage source in the embodiment shown operates at a higher voltage level, for example from 20 volts to 25 volts. Thus, the level shift device 300 shifts the lower voltage level of the incoming control signal ANn to the higher voltage level compatible with the HVDD voltage source.

In operation, the control signal ANn will turn "on" or "off" the transistor device Q1, in effect "closing" or "opening" the switch 210 of FIG. 2. Since the transistor device Q1 serves as a switch, it is designed to have low impedance/resistance when it is turned on (i.e., when the switch is closed). The impedance of the transistor device Q1 needs to be much smaller than the combined impedance of the lead wire 240 (FIG. 2), the electrode contact 250 (FIG. 2), and the target tissue of the patient (which can be simulated as a resistor or an RLC circuit). The dimensions of the transistor device Q1 can be tuned to ensure that it has a low on-resistance. For example, it can be designed to have a high gate width to gate length ratio (W:L or W/L ratio). According to one embodiment, the on-resistance of the transistor device Q1 is in a range from about 10 ohms to about 100 ohms, for example at about 70 ohms.

The transistor devices Q40-Q47 together serve as the current sink 220 of FIG. 2. In more detail, the transistor device Q2 works in conjunction with the transistor devices Q40-Q47 to form a plurality of current mirrors. An externally-supplied reference current I flows through the gate of the transistor device Q2 and establishes a voltage level at its gate. The gates of all the transistor devices Q2 and Q40-Q47 are coupled together. Thus, the reference current I establishes the same voltage level on all the gates of the transistor devices Q2 and Q40-Q47, which causes the FETs of each of the transistor devices Q40-Q47 to attempt to sink the same current (the reference current I) as Q2. As discussed above, the transistor devices Q40-Q47 include different number of FETs. Consequently, the transistor devices Q40-Q47 will attempt to sink different levels of current. For example, since the transistor device Q40 includes only 1 FET, it sinks the reference current I. The transistor device Q43 includes 8 identical FETs, so it sinks 8×I. The transistor device Q47 includes 128 identical FETs, so it sinks 128×I.

The gates of the transistor devices Q30-37 are coupled to an 8-bit binary control signal (or bus) AMPn, which is also generated by the control logic 70 of the microcontroller 50 of FIG. 1. In an embodiment, the transistor device Q30 is coupled to the least significant bit of the control signal AMPn, and the transistor device Q37 is coupled to the most significant bit of the control signal AMPn, so on and so forth.

The drains of the transistor devices Q40-Q47 are coupled to the sources of the transistor devices Q30-Q37, respectively. Therefore, the transistor devices Q30-Q37 serve as current switches that turn on or off depending on the control signal AMPn. The transistor devices Q30-Q37 can be individually turned on or off by the control signal AMPn. In other words, a subset of the transistor devices Q30-Q37 may be turned on, while a different subset of the transistor devices Q30-Q37 may be turned off. Since each of the transistor devices Q30-Q37 is coupled to a respective one of the transistor devices Q40-Q47, the collective current that is drawn by the transistor devices Q40-Q47 (i.e., the current sink 220 of FIG. 2) is tunable and is controlled by the control signal AMPn.

For example, suppose the control signal AMPn has a binary value of 00000111 (decimal value of 7), it will turn on the transistor devices Q30-Q32 and turn off the transistor devices Q33-Q37. As a result, transistor devices Q40-Q42 are sinking current, while the transistor devices Q43-Q47 are not sinking current. The total amount of current sunk by the transistor devices Q40-Q42 is (I+2×I+4×I)=7×I. As another example, suppose the control signal AMPn has a binary value of 10101000 (decimal value of 168), it will turn on the transistor devices Q33, Q35, and Q37 and turn off the remaining transistor devices. As a result, only transistor devices Q43, Q45, and Q47 are sinking current. The total amount of current sunk by the transistor devices Q43, Q45, and Q47 is (8×I+32×I+128×I)=168×I. It can be seen now that by changing the control signal AMPn, the current drawn by the current sink 220 of FIG. 2 (which is implemented with the transistor devices Q30-Q47) can be tuned to vary in amplitude anywhere from 0 (when all the transistor devices Q30-Q37 are turned off) to 255×I (when all the transistor devices Q30-Q37 are turned on). The current amplitude can vary in increments of the reference current I.

It should be understood that different numbers of transistor devices Q30-Q37 could be used, with different numbers of replications M for each, with a corresponding number of transistor devices Q40-Q47 and corresponding numbers of replications M for each. For example, Q30-Q37 could be replaced with 255 transistor devices, each with M=1, and correspondingly Q40-Q47 with 255 transistor devices, also with M=1. In such a system, the control signal AMPn would be thermometer coded instead of binary coded, and would be 255 bits wide. The total current sunk by the transistor devices will be the number of "1" bits in AMPn times I. Thus, the current amplitude can vary in increments of the reference current I. Other arrangements, including but not limited to combinations of thermometer coding and binary coding, are also possible.

Also to ensure proper operation of the circuit, the firmware 60 or control logic 70 (FIG. 1) are designed such that the control signal ANn never turns on the transistor device Q1 when the control signal AMPn is non-zero. Stated differently, when the current sink 220 (FIG. 2) is sinking current, the switch 210 (FIG. 2) should be open. This design makes sure the desired amount of current is pulled through the target tissue area instead of being dumped to the ground needlessly.

In addition, the transistor devices Q30-Q37 are designed to have the same number of FETs as their respectively-coupled transistor devices Q40-Q47 so as to improve linearity of a transfer function from the AMPn binary code to output current.

FIG. 4 is a simplified diagrammatic view of an embodiment of a portion of the neurostimulator device 20 in a stimulation phase (or stimulation cycle) of the operation. The illustrated portion of the neurostimulator device 20 includes four example channels 200A-200D. The channels 200A-200D include switches 210A-210D, current sinks 220A-220D (unidirectional current sources), DC-blocking capacitors 230A-230D (example protective components), and electrode contacts 250A-250D. The electrode contacts 250A-250D are implanted inside different target areas of a patient's tissue 320. In some embodiments, the current sinks 220A-220D and the DC-blocking capacitors 230A-230D may also be implanted in or near the tissue 320. It is also understood that in some embodiments, one of the channels 200A-200D may omit the blocking capacitor.

For the top two channels 200A-200B, their respective switches 210A-210B are programmed to be closed, and their respective current sinks 220A-220B are programmed to be drawing zero current. For the bottom two channels 200C-200D, their respective switches 210C-210D are programmed to be open, and their respective current sinks 220C-220D are programmed to be sinking 1.2 milliamps (mA) and 1.5 mA of current, respectively. It is understood that the numbers used here are merely examples to show that each channel may be programmed to be sinking a different current level, and that any other current level may be programmed depending on the need of the patient. Here, the total amount of current running through the tissue 320 is 2.7 mA. According to Kirchoff's current law, the sum of currents entering a node must equal to a sum of currents leaving that node. Hence, a current $I_1$ flows through the channel 200A (through the capacitor 230A and the electrode contact 250A), and a current (2.7 mA–$I_1$) flows through the channel 200B.

The currents being drawn by the bottom two current sinks 220C-220D generate respective electric fields near their respective electrodes 250C and 250D inside the tissue 320. Depending on the current level, a stronger or weaker electric field is generated, which is correlated to the amount of sensation the patient feels with respect to the target tissue area near the electrode. The top two current sinks 220A-220B are not sinking any current and thus do not provide any stimulation to the patient.

In an embodiment, the channels 200A-200B not sinking current are positioned in close proximity to the channels 200C-200D that sink current. In another embodiment, the channels 200A-200B may be implemented in the hermetically-sealed housing 150 of FIG. 1. It is also understood that although only four channels are shown in FIG. 4, the neurostimulator device 20 may contain any other number of channels similar to the channels 200A-200D, anyone of which is capable of sinking a variable amount of current to stimulate a respective target area of the tissue 320 during the stimulation phase. According to one embodiment, the stimulation phase lasts for about 100 microseconds to about 150 microseconds.

The purpose of the recovery phase is to get an integral of current over the time periods of the stimulation phase and the recovery phase to zero. If the stimulation phase is not accompanied by a recovery phase, the integral of the current (which is the amount of charge) would be non-zero, and this non-zero charge would damage the tissue 320. The recovery phase ensures that no such net charge will be built up. Therefore the recovery phase is implemented to prevent tissue damage. In an embodiment, the recovery phase lasts between about 4 times longer than the stimulation phase and 10 ms. For example, the recovery phase may last for about 400 microseconds to about 10 milliseconds (compared to about 100 microseconds to about 150 microseconds for the stimulation phase). After the recovery phase is complete, the switches are open and the current sinks are set to zero.

The purpose of the recovery phase is to get an integral of current over the time periods of the stimulation phase and the recovery phase to zero. If the stimulation phase is not accompanied by a recovery phase, the integral of the current (which is the amount of charge) would be non-zero, and this non-zero charge would damage the tissue 320. The recovery phase ensures that no such net charge will be built up. Therefore the recovery phase is implemented to prevent tissue damage. In an embodiment, the recovery phase lasts about 4-10 times longer than the stimulation phase. For example, the recovery phase may last for about 400 microseconds to about 1.5 milliseconds (compared to about 100 microseconds to about 150 microseconds for the stimulation phase). After the recovery phase is complete, the switches are open and the current sinks are set to zero.

The patient is not being stimulated during the recovery phase. However, since the stimulation cycle is repeated at a frequency ranging from 15 hertz (Hz) to 300 Hz, such high rate of repetition makes the stimulation feel continuous to the patient. The patient cannot distinguish the stimulation and recovery phases based on his feelings and does not feel any interruptions in the stimulation. In other words, the neurostimulator device 20 provides constant pain relief to the patient throughout its entire operation. It is also understood that the neurostimulator may enter the stimulation phase and the recovery phase in response to pre-set programming instructions embedded in the neurostimulator, or in response to clinician or patient control.

The embodiments of the neurostimulator device 20 discussed above offer advantages over existing neurostimulator devices. It is understood, however, that other embodiments of the neurostimulator device 20 may offer different advantages, and that no particular advantage is required for all embodiments. One of the advantages is reduced chip area consumption and therefore reduced costs. With reference to FIGS. 2 and 3, the current sink 220 shown in FIG. 2 is implemented using the plurality of transistors shown in FIG. 3. For example, the transistor device Q1 is implemented using a PFET, and the transistor devices Q30-Q47 are implemented using 510 NFETs. In other words, implementing a current source similar to the current sink 220 in the transistor level requires a great number of PFETs (or transistors). In some existing bidirectional neurostimulator devices, each channel may include a current source and a current sink, where each one of them may have to be implemented using numerous transistors. The numerous transistors consume integrated circuit chip area and therefore make the neurostimulator device more expensive.

In comparison, the neurostimulator device 20 does not need bidirectional current supplies. Each channel 200 only needs one current sink 220 (unidirectional current source). The switch 210 of FIG. 2 effectively replaces the current sources required for prior devices. Thus, the numerous transistors previously needed to implement the current sources for prior devices can now be replaced by a single transistor that implements the switch 210. In this manner, the number of transistors required to implement each channel 200 of the neurostimulator device 20 is almost halved, and therefore chip area consumption can be greatly reduced. The reduction in chip area in turn leads to lower fabrication costs.

Another advantage offered by the embodiments disclosed above is the capability to use electrodes as "anode guards," which is impossible in previous neurostimulators that require bidirectional current supplies (requiring both a current source and a current sink). Anode guards are electrode contacts that serve as anodes during the stimulation phase, and these electrode contacts also substantially encircle one or more electrode contacts that serve as cathodes. Such configuration helps concentrate the electric field (which stimulates the patient) between the cathode and the encircling anodes and minimize leakage of the electric field beyond the encircling anodes. It is understood that in other embodiments, the cathodes may be partially encircled by the anodes.

The configuration involving anodes and cathodes as discussed above is illustrated in FIG. 6 as an example, which shows a paddle-style lead 400 for spinal cord stimulation. The paddle-style lead 400 is intended to be implanted epidurally following a laminectomy. Electrode contacts 401-416 are located on the paddle-style lead 400. Electrode contacts 403 and 404 are configured as cathodes and are marked with "−" signs. Electrode contacts 402, 405, 408, 409, 410, 413, 414, and 415 are configured as anodes and are marked with "+" signs. As is shown, the anode 402, 405, 408, 409, 410, 413, 414, and 415 serve as anode guards and encircle the cathodes 403-404. These anodes 402, 405, 408, 409, 410, 413, 414, and 415 are respectively coupled to a power supply rail (such as the voltage source HVDD of FIG. 4) via respective switches (such as the switch 210 of FIG. 4). It must be understood that some in the industry use the opposite convention for indicating cathodes and anodes, that is to say, they indicate cathodes with "+" signs and anodes with "−" signs. The convention of marking used is not relevant to the operation of the neurostimulator according to various aspects of the present disclosure.

The channels associated with the anodes 402, 405, 408, 409, 410, 413, 414, and 415 are referred to as anodic channels, which do not sink current during the stimulation phase. Thus, the anodic channels are similar to the channels 200A and 200B of FIG. 4. The channels associated with the cathodes 403-404 are referred to as cathodic channels, which do sink current during the stimulation phase. Thus, the cathodic channels are similar to the channels 200C and 200D of FIG. 4.

In order to minimize the leakage beyond these anodes and to concentrate the electric field between the cathodes and the anodes, it is desirable for the anodes to all be at the same electric potential. In previous neurostimulator devices requiring bidirectional current supplies, it is extremely unlikely that the anodes will all be at the same potential. Since a bidirectional-current-supply neurostimulator controls the currents through each anode, the anodes will be at the same potential only if the current on each anode happens to have the right value to match the impedance between the anodes and cathodes. Since that impedance varies over time for various reasons, this is not likely to happen.

Other previous neurostimulators may have only a single current source and can switch each electrode contact to "anode", "cathode", or "off". In such neurostimulators, all of the anodes may be at the same potential, because they are connected to the same side of the single current source. However, because that type of stimulator has only one current source, it cannot control the currents through the cathodes, thereby diminishing its flexibility and usefulness.

Figure 6:
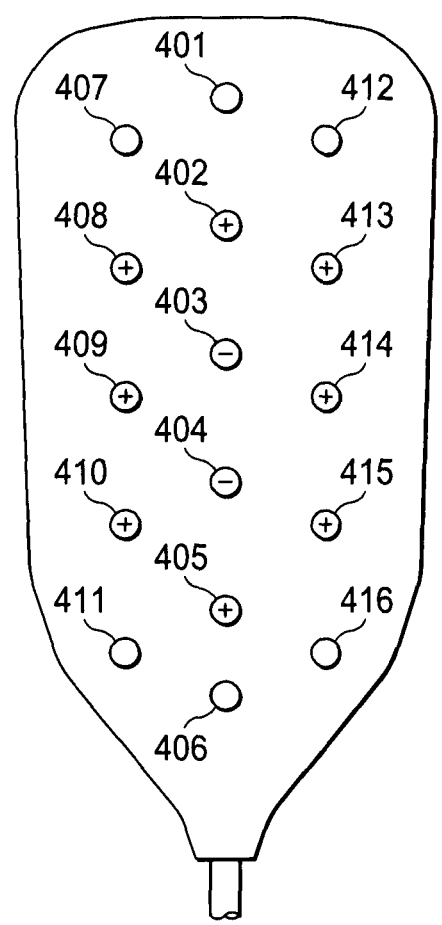
FIG. 6 is a simplified diagrammatic view of an embodiment of a paddle lead showing placements of anodes and cathodes of a neurostimulator device.

In contrast, the neurostimulator device 20 discussed above couples all of its anode contacts to the high-voltage power rail (such as HVDD). Therefore, the anodes 402, 405, 408, 409, 410, 413, 414, and 415 are inherently all at the same potential and function well as anode guards. At the same time, the neurostimulator device 20 still has configurable current sinks for every cathode, which permits the further adjustment of the electric field within the guard ring to target specific areas within the tissue 320. It is understood that FIG. 6 is only an example, and that similar or alternative configurations are possible with other electrode contact configurations on a paddle lead similar to the paddle lead 400 or with other types of leads, with analogous benefits associated with the embodiments of the present disclosure.

The following Figures and paragraphs involve several alternative embodiments of the neurostimulator device 20. For the sake of clarity and consistency, similar components in the following Figures will be labeled the same as they appear in FIGS. 1-6.

FIG. 7 illustrates a simplified diagrammatic view of an embodiment of a portion of the neurostimulator device 20 in the stimulation phase of the operation. Similar to FIG. 4, FIG. 7 includes channels 200A-200D. Unlike FIG. 5, however, all of the switches 210A-210D are open in FIG. 7. Furthermore, FIG. 7 includes an additional channel 200E. The channel 200E does not include a current sink, but it does include a programmable switch 210E that is closed, as well as a DC-blocking capacitor 230E and an electrode contact 250E that is implanted in the tissue 320.

The channel 200E may represent the above-mentioned hermetically-sealed housing 150 of FIG. 1. Since the current sinks 220C and 220D sink 1.2 mA and 1.5 mA of current, respectively, the total amount of current flowing through the channel 200E and into the tissue 320 is 2.7 mA. As discussed above, the patient only feels stimulation in areas where the channel is sinking current, which in this example include channels 200C-200D. The channel 200E is provided to satisfy Kirchoff's current law, but it does not stimulate the patient. Meanwhile, the channels 200A-200B are effectively nonexistent, since they are neither sourcing current to the channels 200C-200D nor sinking current themselves.

Figure 8:
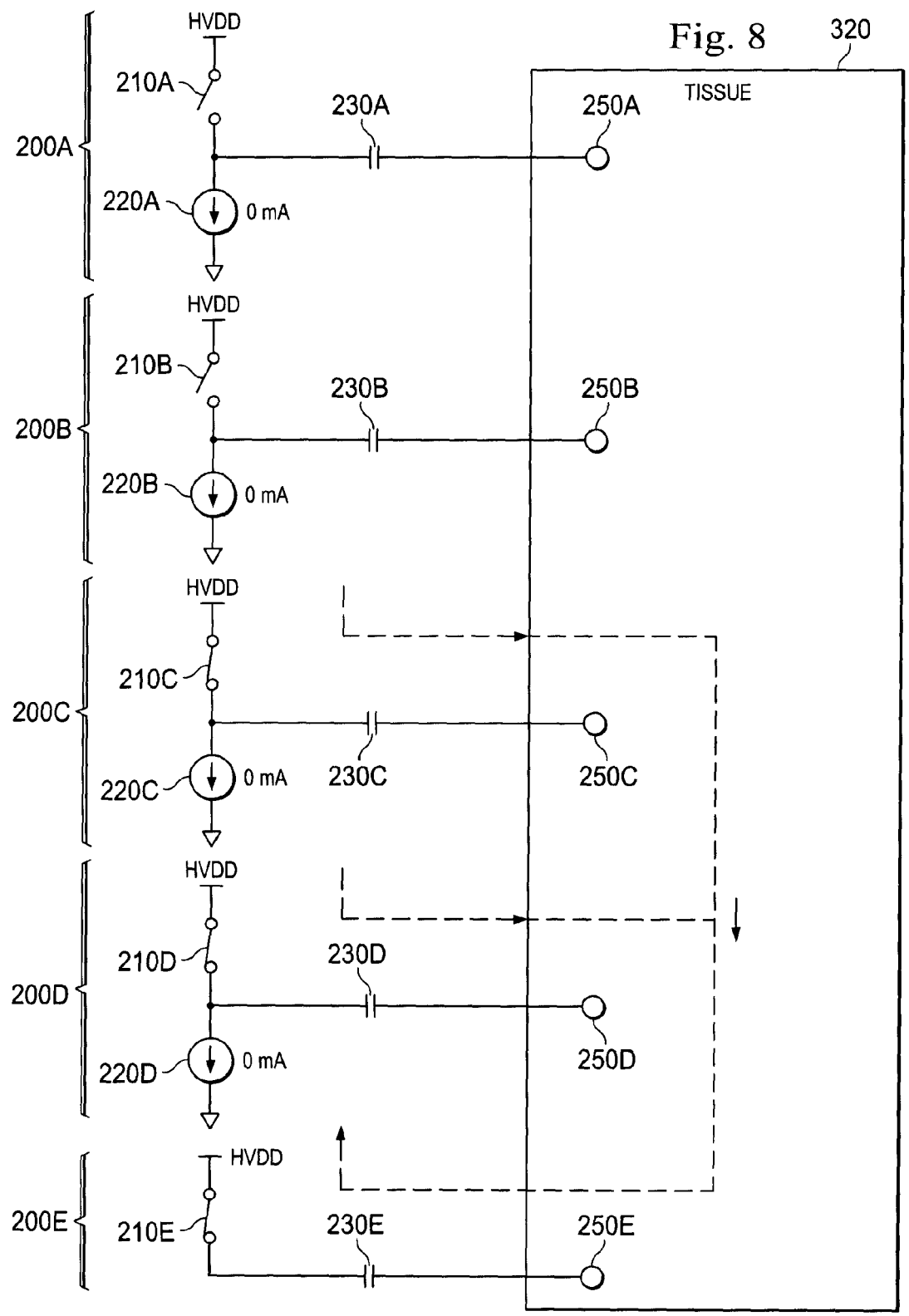

FIG. 8 shows the circuit of FIG. 7 in the recovery phase. Here, the switches 210A-210B are still open, but the switches 210C-210E are closed. None of the current sinks 220A-220D are sinking current. The charges built up on the capacitors 230C-230D during the stimulation phase are discharged via the channel 200E. As discussed above, this discharging of the capacitors 230C-230D ensures a current integral of about zero over the stimulation phase and the recovery phase, thereby preventing tissue damage.

In some embodiments, the switches 210A-210B may be closed in the recovery phase. Such configuration may help remove any charge developed by leakage currents and may also help simplify the control logic.

Figure 9:
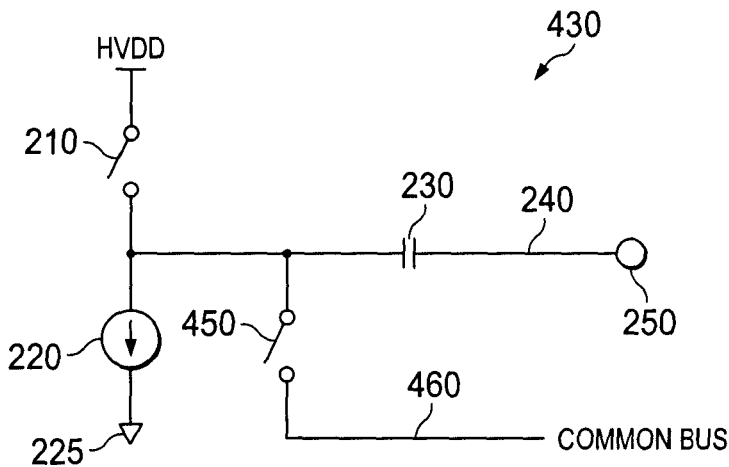
FIG. 9 is a simplified circuit level view of another alternative embodiment of a channel of a neurostimulator device.

FIG. 9 is a simplified diagrammatic view of another alternative embodiment of a channel 430 of the neurostimulator device 20. The channel 430 includes similar components as the channel 200 of FIG. 2, and these similar components are labeled the same in FIG. 9 for the sake of clarity and consistency. In addition, the channel 430 includes a charge balance switch 450 having one end coupled to the current sink 220 and the protective component 230, and having the other end coupled to a common bus 460. In an embodiment, the common bus 460 is electrically floating. In another embodiment, the common bus 460 is tied to a voltage reference such as the circuit ground. Though not illustrated, it is understood that the additional channels each include a charge balance switch similar to the switch 450, and all these charge balance switches are coupled to the common bus 460. Thus, when the charge balance switches (including the switch 450) are closed, all the channels are coupled to the common bus through which current can flow to equalize the voltage across all of the capacitors (i.e., capacitors similar to the DC-blocking capacitor 230).

Figure 10:
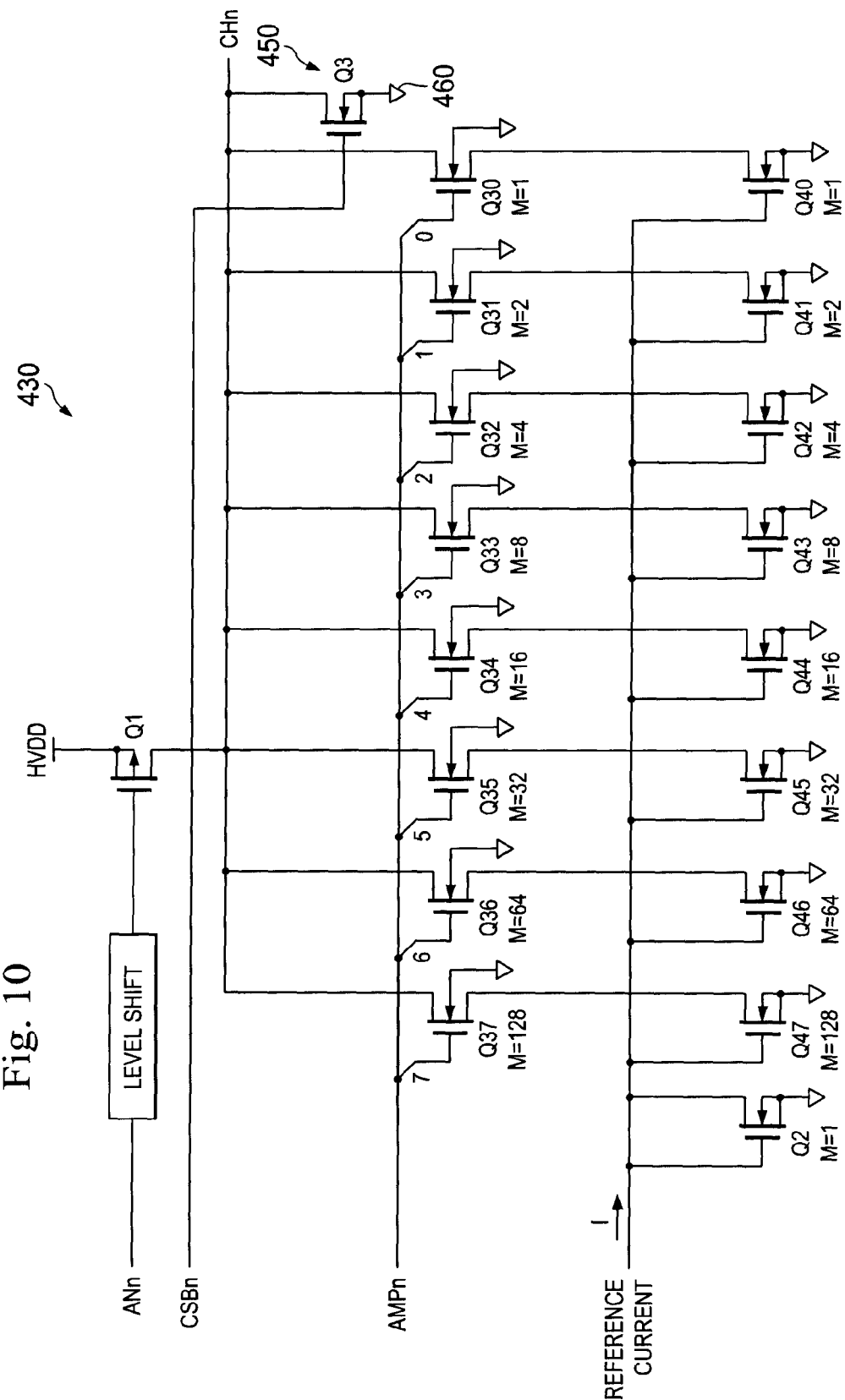
FIG. 10 is a simplified transistor level view of an alternative embodiment of the channel shown in FIG. 9.

FIG. 10 is an example transistor circuit level view of the channel 430 of FIG. 9. The protective component 230, the lead wire 240, and the electrode contact 250 are omitted from FIG. 10 for the sake of simplicity. The configuration and operation of the circuit shown in FIG. 10 is similar to what was shown in FIG. 3 and therefore are not repeated for the sake of simplicity. Unlike the circuit shown in FIG. 3, however, is that the circuit includes the charge balance switch 450 of FIG. 9, which is implemented as the transistor device Q3.

The transistor device Q3 includes an NFET whose gate is coupled to a control signal CSBn that is supplied by the control logic 70 of the microcontroller 50 of FIG. 1. The control signal CSBn either turns the transistor device Q3 on or off, thereby making it behave like a programmable switch. The drain of the transistor device Q3 is coupled to the drain of the transistor device Q1 (which is the implementation of the switch 210 of FIG. 9). The source of the transistor device Q3 is coupled to the common bus 460, which as discussed above may be tied to the electrical ground, as shown in FIG. 10, or it may be electrically floating.

Figure 11:
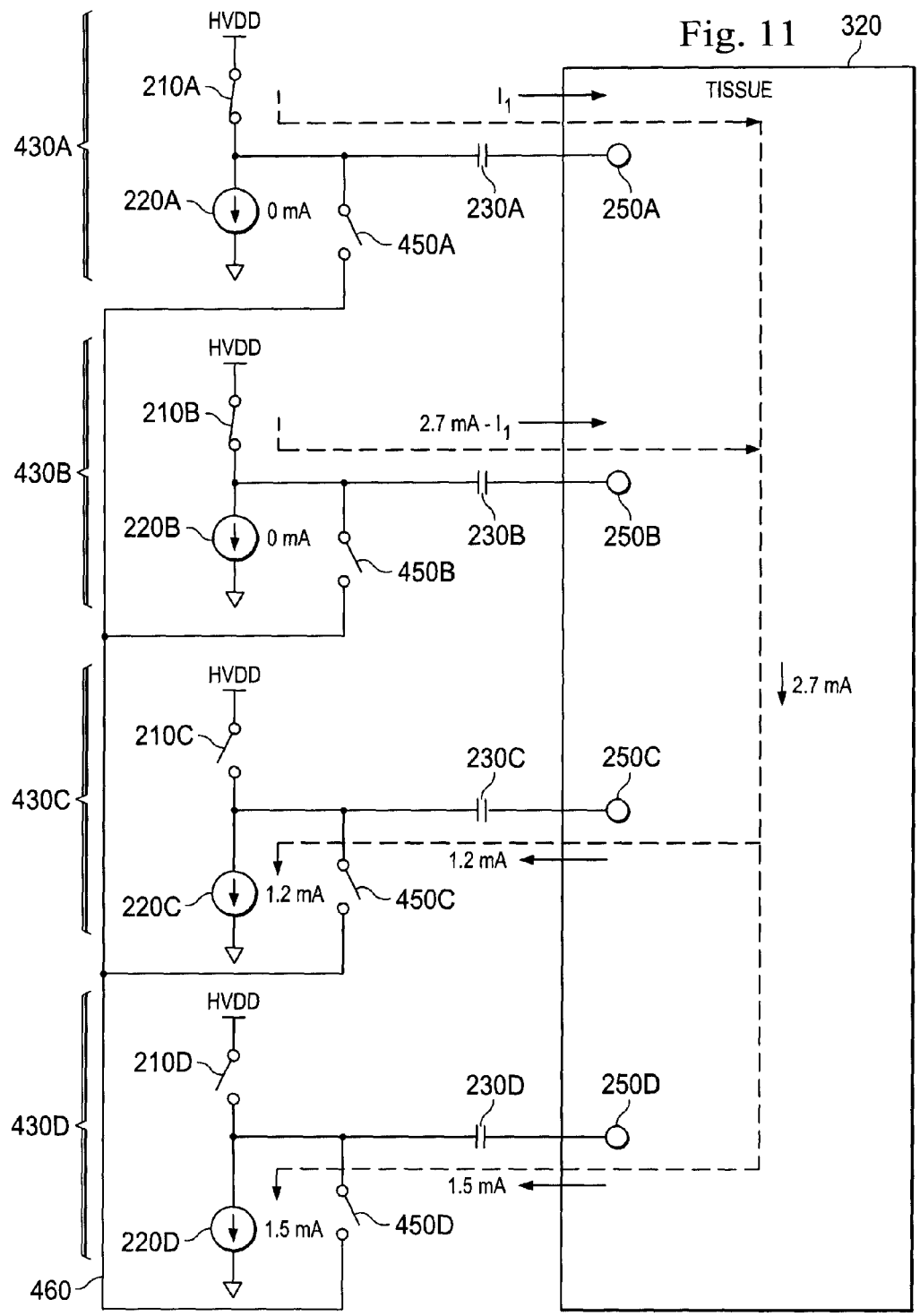
FIGS. 11-12 are simplified circuit level views of a plurality of channels of a neurostimulator device in a stimulation phase and a recovery phase of an operation, respectively, according to the alternative embodiment shown in FIGS. 9-10.
Figure 12:
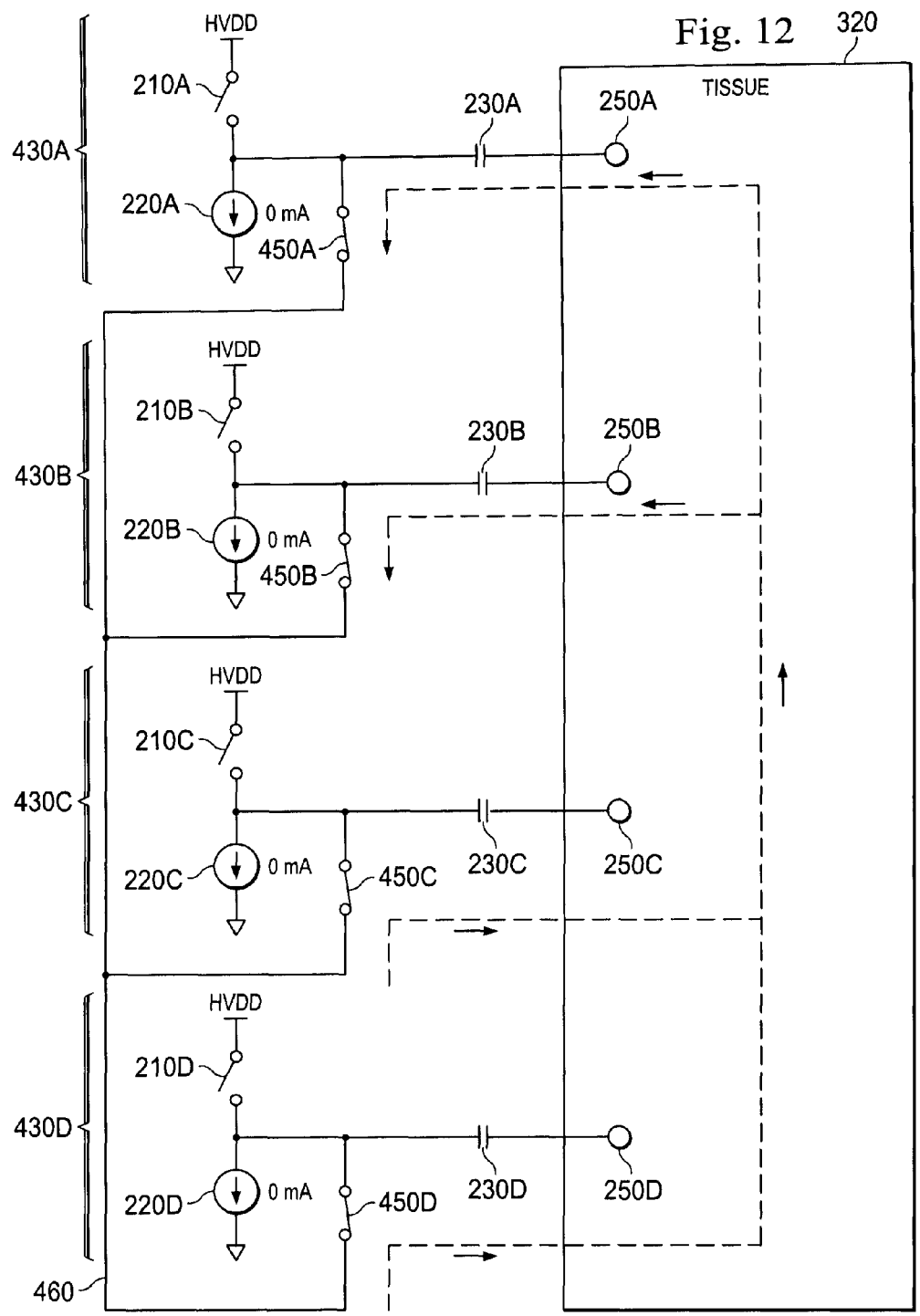

FIGS. 11-12 are simplified diagrammatic views of the alternative embodiment including the charge balance switch during the stimulation and recovery phases, respectively. Referring to FIG. 11, the configuration of the circuits is similar to what is shown in FIG. 4. In other words, the channels 430C-430D are sinking currents, while the channels 430A-430B are working together to source the currents sunk by the channels 430C-430D. In addition, the charge balance switches 450A-450D are provided and coupled to the DC-blocking capacitors 230A-230D and the common bus 460. The charge balance switches 450A-450D are all open during the stimulation phase. The patient receives stimulation from the channels 430C-430D, but not from channels 430A-430B.

Referring now to FIG. 12, the circuit in FIG. 11 is in the recovery phase. The current sinks 220A-220D are all programmed to be sinking no current. The switches 210A-210D are all open, but the charge balance switches 450A-450D are all programmed to be closed. The charges stored on the DC-blocking capacitors 230C-230D are discharged through the channels 430A-430B to ensure that the integral of current over time is still zero. It is understood that in some embodiments, one of the channels 430A-430D may omit the DC-blocking capacitor.

In addition to the advantages discussed above, the alternative embodiment shown in FIGS. 9-12 offer other advantages. One advantage is increased design flexibility. In some applications, it may be desirable to limit the peak current flow during the recovery phase. The charge balance switches 450A-450D can be sized differently from other switches (such as switches 210A-210D) to have higher resistance than these other switches. The higher resistance will help limit the peak current flow. Another advantage is reduced leakage. In the real world, unwanted parasitic impedances are present in the circuits shown above (for example, the circuits in FIGS. 2 and 9). These parasitic impedances may cause current or voltage leakages, which reduces the effectiveness of the neurostimulator device 20. Therefore, it may be desirable to ground the side of the capacitor 230 coupled to the current sink 220 in order to reduce the effects of leakage through parasitic impedances. Here, the common bus 460 can be tied to ground to provide the grounding of the capacitor 230, so that the leakage effects can be alleviated.

It is also understood that in some embodiments, the neurostimulator device can be programmed to operate in either the mode with the charge balance switch 450, or the mode without it. Furthermore, in another alternative embodiment, the neurostimulator device 20 may include the charge balance switches 450 as well as a channel needing no current sinks (i.e., the hermetically-sealed housing 150). In other words, the embodiment discussed above in FIGS. 9-12 may be combined with the embodiment discussed above in FIGS. 7-8.

Figure 13:
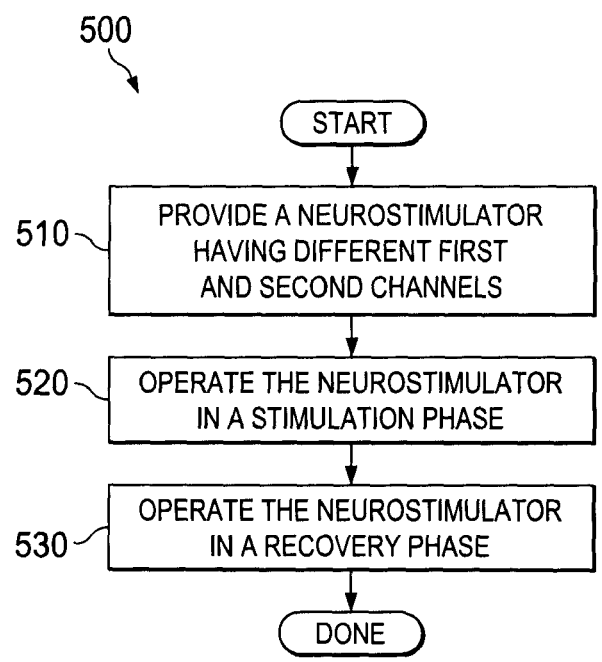
FIG. 13 is a flowchart illustrating a method involving the neurostimulator device according to various aspects of the present disclosure.

FIG. 13 illustrates a flowchart of a method 500 involving the neurostimulator device 20. The method 500 includes block 510 in which a neurostimulator having different first and second channels is provided. The first channel includes a first tunable unidirectional current source. The first and second channels also include respective first and second switches each coupled to a power supply, wherein the first current source is coupled to the power supply through the first switch. The first and second channels also include respective first and second electrodes coupled to the first and second switches, respectively. The method 500 continues with block 520 in which the neurostimulator enters a stimulation phase by: opening the first switch; closing the second switch; and tuning the first current source in a manner such that it sinks a programmable amount of electrical current. The method 500 continues with block 530 in which the neurostimulator enters a recovery phase by: closing both the first and second switches; and tuning the first current source in a manner such it does not sink any electrical current.

Figure 14B:
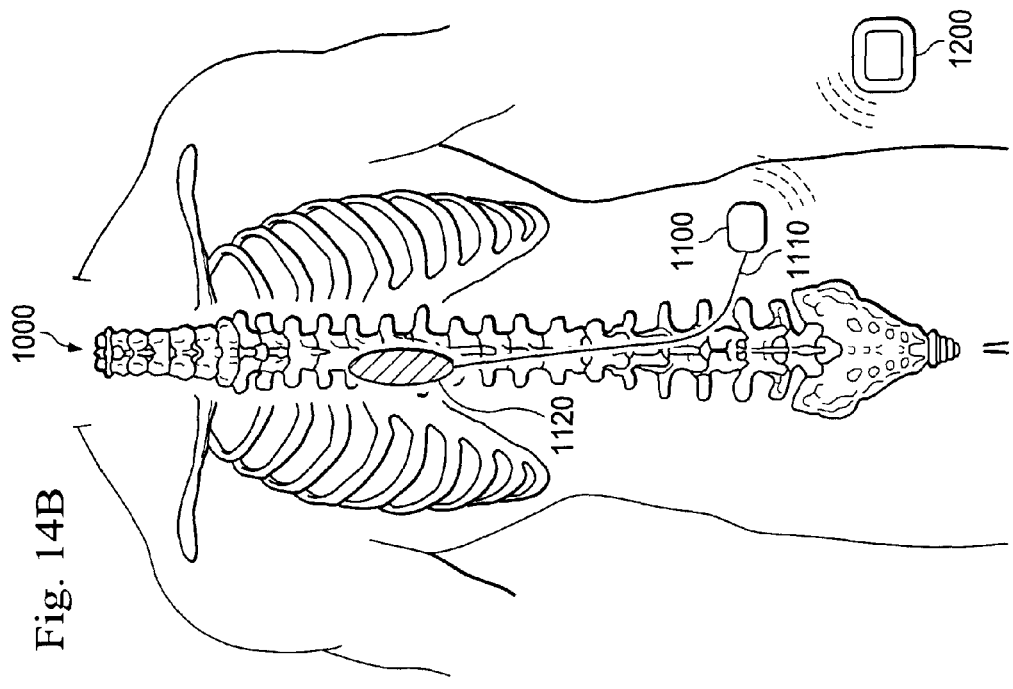
FIGS. 14A and 14B are side and posterior views of a human spine, respectively.
Figure 14A:
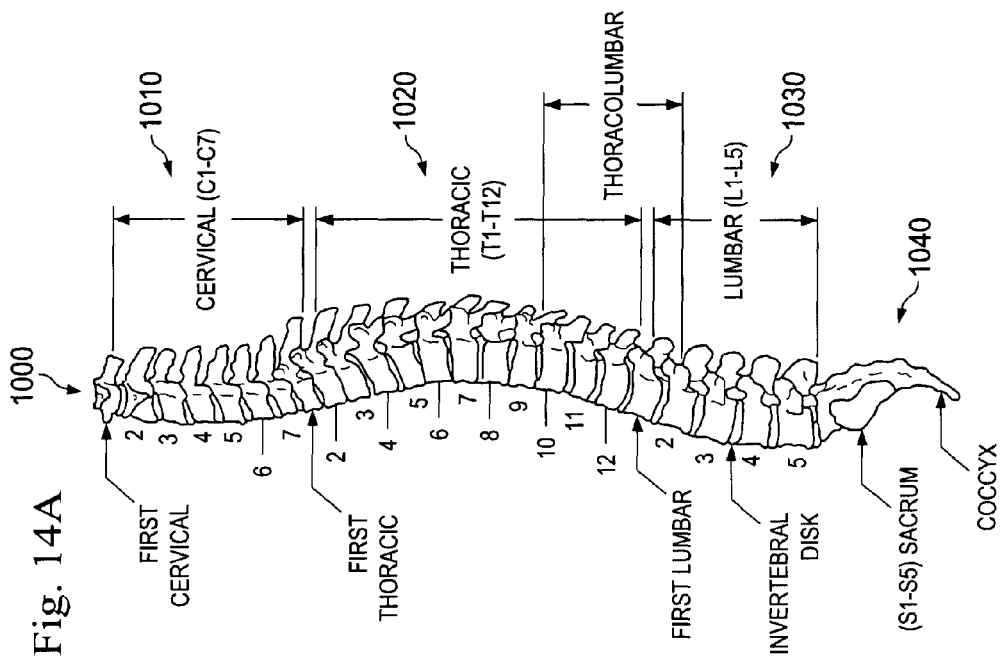

FIG. 14A is a side view of a spine 1000, and FIG. 14B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 14B, an IPG device 1100 is implanted inside the body. The IPG device 1100 may include various embodiments of the neurostimulator device 20 described above. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200.

The IPD device 1100 may be set in a trialing mode to test different groups of stimulation patterns. For example, in an embodiment, a paddle-style lead (such as the one shown in FIG. 6) is used as a lead to stimulate the neural tissue. The paddle-style lead has a plurality of electrodes that can each be programmably set as a cathode or an anode. The patient or the clinician may programmably enter a first stimulation pattern, in which a subset of electrodes on the lead are designated as cathodes, and a different subset of electrodes on the lead are designated as anodes. In accordance with the discussions associated with FIG. 6 above, the group of anodes may at least partially encircle the cathodes so as to minimize leakage of the electric field beyond the encircling anodes. The current flow between the anodes and the cathodes serves to electrically stimulate a desired adjacent area of neural tissue by generating an electric field in the tissue. The selection of the cathode and anode subset may be made to minimize electric field leakage and thus reduce stimulation of undesired areas of neural tissue.

These anodes on the lead all receive a steady voltage delivered by the voltage supply (e.g., HVDD) and may all have substantially identical voltage potentials. The cathodes on the lead are coupled to their respective current sinks and therefore may have different potentials than the anodes or from one another. The cathodes serve to electrically stimulate a desired adjacent area of neural tissue by generating electric fields through the current drawn from the current sinks. Meanwhile, the anodes are serving as "anode guards" to minimize electric field leakage.

The patient may then decide to try a second stimulation pattern that is different from the first stimulation pattern. The second stimulation pattern sets different groups of electrodes as anodes and cathodes than the first stimulation pattern. The cathodes of the second stimulation pattern will carry out electrical stimulation of a different area of the neural tissue, while the anodes still serve as anode guards for these cathodes. The patient may decide whether the first stimulation pattern or the second stimulation pattern is better. He may also try an additional number of different stimulation patterns until he finds the one he prefers.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A medical device, comprising:
   a neurostimulator that includes one or more channels, wherein each channel includes:
   a digitally-controlled switch coupled to a voltage source, wherein the switch is in one of: an "on" state and an "off" state in response to a first control signal;
   a digitally-controlled current sink coupled to the switch in a manner such that the switch is coupled between the current sink and the voltage source, wherein the current sink is electrically isolated from the voltage source when the switch is in the "off" state, and wherein the current sink draws a variable amount of electrical current in response to a second control signal, and wherein the second control signal includes a plurality of bits, and wherein the current sink includes a plurality of first transistors and a plurality of second transistors, wherein the first transistors are each coupled to the switch through a respective one of the second transistors, wherein the first transistors are each operable to draw a current that is an integer multiple of a reference current, and wherein the second transistors are operable to be individually turned on or off by a corresponding bit of the second control signal, thereby enabling the respectively-coupled first transistor to draw current or preventing such first transistor from drawing current; and
   a conductor coupled to the switch and the current sink, wherein the conductor is configured to be coupled to an electrode that is operable to deliver the electrical current drawn by the current sink to a target tissue area.

2. The medical device of claim 1, wherein each channel further includes a capacitor that is operable to filter out a direct current (DC) component in the electrical current delivered by the electrode.

3. The medical device of claim 1, wherein the neurostimulator further includes:
   power circuitry that supplies the voltage source;
   transceiver circuitry that facilitates communication with one or more external devices; and
   control circuitry that generates the first and second control signals in response to the communication with the one or more external devices.

4. The medical device of claim 3, wherein the control circuitry is operable to generate and send different versions of the first and second control signals to each of the channels in a manner so that a subset of the channels are turned on while a different subset of the channels are turned off.

5. The medical device of claim 3, wherein the control circuitry generates the first and second control signals in a manner such that the switch is never turned on when the current sink is drawing current.

6. The medical device of claim 1, further including a charge balance switch coupled between the current sink and a common bus, the common bus being tied to one of: a floating node, a voltage reference, and an electrical ground.

7. A method, comprising:
   providing a neurostimulator having different first and second channels, the first channel including a first tunable unidirectional current source, the first and second channels also including:
   respective first and second switches each coupled to a power supply, wherein the first current source is coupled to the power supply through the first switch; and respective first and second electrodes coupled to the first and second switches, respectively;
entering a stimulation phase by:
opening the first switch;
closing the second switch; and
tuning the first current source in a manner such that it sinks a programmable amount of electrical current; and
entering a recovery phase by:
closing both the first and second switches; and
tuning the first current source in a manner such that it does not sink any electrical current.

8. The method of claim 7, wherein the providing the neurostimulator is carried out in a manner such that the second channel further includes a second tunable unidirectional current source that is operable to sink a different amount of electrical current than the first current source;
wherein the entering the stimulation phase further includes tuning the second current source in a manner such that it sinks no electrical current during the stimulation phase; and
wherein the entering the recovery phase further includes tuning the second current source in a manner such that it sinks no electrical current during the recovery phase.

9. The method of claim 7, wherein the providing the neurostimulator is carried out in a manner such that the first channel includes a direct current (DC) blocking capacitor; and
wherein the recovery phase is carried out in a manner such that the DC blocking capacitor discharges during the recovery phase.

10. The method of claim 7, wherein the enter the stimulation phase and the entering the recovery phase are carried out in a manner such that an operating period for the recovery phase is at least multiple times longer than an operating period for the stimulation phase.

11. An electrical stimulation device, comprising:
a voltage supply means for delivering a steady voltage;
a switching means for selectively opening and closing a circuit path coupled to the voltage supply means;
a current sink means for sinking a programmably-adjustable amount of current, the current sink means being coupled to the voltage supply means through the switching means, wherein the opening of the circuit path cuts off electrical coupling between the current sink means and the voltage supply means, wherein the current sink means includes: a plurality of current mirror means for sinking currents that are different integer multiples of a reference current, and a plurality of current mirror switch means for selectively allowing a subset of the current mirror means to sink current while preventing a different subset of the current mirror means from sinking current; wherein each of the current mirror means is coupled to a respective one of the current mirror switch means; and
a conductor means for stimulating a living body, the conductor means being coupled to both the switching means and the current sink means.

12. The electrical stimulation device of claim 11, further including an electrode means for carrying out the stimulating of the living body by delivering current drawn from the current sink means to a designated region of the body, the electrode means being coupled to the conductor means.

13. The electrical stimulation device of claim 12, further including a protective means for removing a direct current (DC) component from the current delivered to the body, the protective means being coupled between the electrode means and the current sink means.

14. The electrical stimulation device of claim 11, further including a microcontroller means for:
putting the switching means in one of: an "open" state and a "closed" state; and
setting the amount of current sunk by the current sink means.

15. The electrical stimulation device of claim 14, further including a plurality of additional current sink means being coupled to the voltage supply means through a respective additional switching means;
wherein the microcontroller means is operable to:
put a subset of the switching means to the "open" state while putting a different subset of the switching means to the "closed" state; and
set a subset of the current sink means to sink a respective amount of current while setting a different subset of the current sink means to sink no current.

16. An electrical stimulation device, comprising:
a plurality of anodic channels that each include an anode electrode coupled to a steady voltage supply; and
a cathodic channel that includes a current sink that sinks a programmably-determined amount of current and a cathode electrode coupled to the current sink;
wherein the anode electrode and the cathode electrode are both implemented on a lead that is operable to carry out electrical stimulation of a neural tissue, wherein the anode electrodes of the plurality of the anodic channels are positioned on the lead in a manner such that the cathode electrode is at least partially encircled by the anode electrodes, and wherein all the anode electrodes have identical voltage potentials.

17. The electrical stimulation device of claim 16, wherein the lead includes a paddle-style lead.

18. The electrical stimulation device of claim 16, wherein:
the anodic channel and the cathodic channel each include a programmable switch through which the anode electrode and the cathode electrode are each coupled to the voltage supply;
the switch of the anodic channel is programmed to be in a closed position; and
the switch of the cathodic channel is programmed to be in an open position.

19. The electrical stimulation device of claim 18, wherein:
the current sink of the cathodic channel is coupled to the voltage supply through the open-position switch of the cathodic channel;
the anodic channel includes a current sink that is coupled to the voltage supply through the closed-position switch of the anodic channel; and
the current sink of the anodic channel sinks no current while the current sink of the cathodic channel sinks a non-zero amount of current.

20. The electrical stimulation device of claim 16, further including a microcontroller that is operable to:
program the amount of current sunk by the current sink of the cathodic channel;
set the switch of the anodic channel to be in the closed position; and
set the switch of the cathodic channel to be in the open position.

21. The electrical stimulation device of claim 16, wherein:
the anodic channel includes a direct-current-blocking capacitor that is coupled between the anode electrode and the voltage supply; and the cathodic channel includes a direct-current-blocking capacitor that is coupled between the cathode electrode and the current sink.

* * * * *